US012797225B2

(12) United States Patent
Derrico et al.

(10) Patent No.: US 12,797,225 B2
(45) Date of Patent: Nov. 17, 2026

(54) TRAUMA COLLAR

(71) Applicant: Trend Medical, LLC, Bethlehem, PA (US)

(72) Inventors: Blaise Derrico, Breinigsville, PA (US); Brandon Boyer, Breinigsville, PA (US)

(73) Assignee: Trend Medical, LLC, Bethlehem, PA (US)

( * ) Notice: Subject to any disclaimer, the term of this patent is extended or adjusted under 35 U.S.C. 154(b) by 0 days.

(21) Appl. No.: 18/844,520

(22) PCT Filed: Mar. 8, 2023

(86) PCT No.: PCT/US2023/063913
§ 371 (c)(1),
(2) Date: Sep. 6, 2024

(87) PCT Pub. No.: WO2023/172944
PCT Pub. Date: Sep. 14, 2023

(65) Prior Publication Data

US 2025/0186238 A1 Jun. 12, 2025

Related U.S. Application Data

(60) Provisional application No. 63/477,413, filed on Dec. 28, 2022, provisional application No. 63/318,245, filed on Mar. 9, 2022.

(51) Int. Cl.
*A61F 5/055* (2006.01)

(52) U.S. Cl.
CPC .................................... *A61F 5/055* (2013.01)

(58) Field of Classification Search
CPC .... A61F 5/055; A61F 5/05883; A61F 5/3707; A43C 11/16; A43C 11/165; A44B 11/00;
(Continued)

(56) References Cited

U.S. PATENT DOCUMENTS 4,271,999 A * 6/1981 Stravitz .................... G10G 5/00
24/666
5,230,698 A * 7/1993 Garth ...................... A61F 5/055
602/18
(Continued)

FOREIGN PATENT DOCUMENTS

CN 205698178 U 11/2016
IN 348456001 10/2021
(Continued)

OTHER PUBLICATIONS

"JMS Med Supply: Trend Trauma Collar L0174/L0180." Found online Apr. 12, 2024 at jmsmedsupply.com. Reference dated Feb. 7, 2023. Retrieved from https://jmsmedsupply.com/products/trend-trauma-collar-10180, 1 page.
(Continued)

*Primary Examiner* — Kari K Rodriquez
(74) *Attorney, Agent, or Firm* — Saul Ewing LLP; Brian R. Landry

(57) ABSTRACT

One aspect of the invention provides an adjustable cervical collar including a chest piece adapted and configured to rest against a subject's sternum. The adjustable cervical collar also includes a back piece adapted and configured to rest on a posterior surface of the subject's neck and couple to the chest piece. The adjustable cervical collar also includes a chin support movably coupled to the chest piece. The adjustable cervical collar also includes a first shaft assembly and a second shaft assembly each rotatably mounted on a opposing lateral regions of the chest piece. The first shaft assembly and a second shaft assembly each includes: a helically threaded portion engaged with the chin support such that rotation of the helically threaded shaft causes the chin support to raise and lower: a bendable portion coupled
(Continued)

to the helically threaded portion; and a geared portion coupled to the bendable portion.

15 Claims, 13 Drawing Sheets

(58) Field of Classification Search
CPC ... A44B 11/25; A44B 11/258; A44B 11/2584; A44B 11/2592
See application file for complete search history.

(56) References Cited

U.S. PATENT DOCUMENTS

| | | | | |
|---|---|---|---|---|
| 5,632,722 | A | 5/1997 | Tweardy et al. | |
| D592,310 | S | 5/2009 | Leatt | |
| D605,300 | S | 12/2009 | Mazzarolo | |
| D631,167 | S | 1/2011 | Leatt | |
| D647,623 | S | 10/2011 | Thorgilsdottir | |
| D662,597 | S | 6/2012 | Chang | |
| D666,302 | S | 8/2012 | Joseph | |
| D692,568 | S | 10/2013 | Chiang | |
| D693,014 | S | 11/2013 | Chiang | |
| D948,062 | S | 4/2022 | Chang | |
| D1,013,880 | S | 2/2024 | Wang | |
| 2002/0095750 | A1* | 7/2002 | Hammerslag | A43B 5/16 24/68 SK |
| 2004/0176713 | A1 | 9/2004 | Garth | |
| 2007/0027418 | A1 | 2/2007 | Calco et al. | |
| 2007/0270728 | A1 | 11/2007 | Chao | |
| 2013/0060179 | A1* | 3/2013 | Modglin | A61F 5/01 602/18 |
| 2013/0281900 | A1* | 10/2013 | Suarez | A61F 5/055 602/18 |
| 2014/0107551 | A1* | 4/2014 | Modglin | A61F 5/055 602/18 |
| 2015/0216708 | A1* | 8/2015 | Garth | A61F 5/055 602/18 |
| 2020/0368056 | A1* | 11/2020 | Doty | A61F 5/05883 |
| 2021/0228396 | A1 | 7/2021 | Zimmer | |
| 2023/0272138 | A1* | 8/2023 | Lisalova | G01N 33/54393 435/7.1 |
| 2024/0225883 | A1* | 7/2024 | Li | A61F 5/055 |
| 2024/0252339 | A1* | 8/2024 | Cowart | A61F 5/055 |
| 2025/0302655 | A1* | 10/2025 | Price | A61F 5/055 |
| 2026/0053657 | A1* | 2/2026 | Unnsteinsson | A61F 5/01 |
| 2026/0151251 | A1* | 6/2026 | Wang | A61F 5/055 |

FOREIGN PATENT DOCUMENTS

| | | |
|---|---|---|
| KR | 20190110692 A | 10/2019 |
| KR | 301205288 | 2/2023 |

OTHER PUBLICATIONS

"Laerdal: Stifneck Select Adult Adjustable Collar." Found online Apr. 12, 2024 at amazon.com. Reference dated May 16, 2006. Retrieved from https://www.amazon.com/Laerdel-Stifneck-Select-Adjustable-Colar/dp/B00NTSFH94/ , 1 page.
"Orthomen: Cervical Collar by Orthomen." Found online Apr. 12, 2024 at youtube.com. Reference dated Nov. 4, 2022. Retrieved from https://www.youtube.com/watch?v=9bkA98Mg1rU , 1 page.
"Risurry: Cervical Neck Traction Device Neck Brace for Men and Women." Found online Apr. 12, 2024 at amazon.com. Reference dated Feb. 1, 2024. Retrieved from https://www.amazon.com/dp/B0CTMKPTNL , 1 page.
International Search Report and Written Opinion, International Patent Application No. PCT/US2023/063913, Jun. 15, 2023.

* cited by examiner

DETAIL B

DETAIL C

TRAUMA COLLAR

CROSS-REFERENCE TO RELATED APPLICATIONS

The present application is a 35 U.S.C. § 371 national phase application from, and claims priority to, PCT International Patent Application No. PCT/US2023/063913, filed Mar. 8, 2023, which claims priority to U.S. Provisional Patent Application No. 63/318,245, filed Mar. 9, 2022, and U.S. Provisional Patent Application No. 63/477,413, filed Dec. 28, 2022, which are incorporated herein by reference in their entirety.

BACKGROUND OF THE INVENTION

Trauma collars or neck braces serve a variety of purposes. They can stabilize the neck after cervical spine surgery, or they can provide non-surgical relief after a trauma or injury to the neck. A major problem associate with the use of trauma collars is disturbance to the neck of the subject when the collar is place on the subject. This disruption can exacerbate the injury or discomfort of the subject.

SUMMARY OF THE INVENTION

One aspect of the invention provides an adjustable cervical collar. The adjustable cervical collar includes a chest piece adapted and configured to rest against a subject's sternum. The adjustable cervical collar also includes a back piece adapted and configured to rest on a posterior surface of the subject's neck and couple to the chest piece. The adjustable cervical collar also includes a chin support movably coupled to the chest piece. The adjustable cervical collar also includes a first shaft assembly and a second shaft assembly each rotatably mounted on a opposing lateral regions of the chest piece. The first shaft assembly and a second shaft assembly each includes: a helically threaded portion engaged with the chin support such that rotation of the helically threaded shaft causes the chin support to raise and lower; a bendable portion coupled to the helically threaded portion; and a geared portion coupled to the bendable portion on an opposite end relative to the helically threaded portion. The adjustable cervical collar also includes an adjustment knob positioned on the chest piece and coupled to the geared portion of each of the first shaft assembly and the second shaft assembly.

This aspect of the invention can have a variety of embodiments. The adjustment knob can be coupled to a bevel gear complementary to the geared portion of the first shaft assembly and the second shaft assembly. The bevel gear and the adjustment knob can each include complementary splines that allow the adjustment knob to slide axially with respect to the bevel gear.

The adjustment knob and the chest piece further include complementary detents, wherein the complementary detents can be: engaged to lock by moving the adjustment knob toward the subject's sternum; and disengaged to allow rotation by moving the adjustment knob away from the subject's sternum.

The back piece can include at least one relief, the relief being configured to provide flexibility to the back piece. The back piece can include a plurality of reliefs.

One or more of the first shaft assembly, the second shaft assembly, and the adjustment knob can be located externally to one or more of the chest piece and the back piece.

Another aspect of the invention provides an adjustable cervical collar. The adjustable cervical collar includes a chest piece adapted and configured to rest against a subject's sternum. The adjustable cervical collar also includes a back piece adapted and configured to rest on a posterior surface of the subject's neck and couple to the chest piece. The adjustable cervical collar also includes a chin support movably coupled to the chest piece. The adjustable cervical collar also includes a first shaft assembly and a second shaft assembly each rotatably mounted on a opposing lateral regions of the chest piece. The first shaft assembly and a second shaft assembly each include: a threaded portion engaged with the chin support such that rotation of a threaded shaft causes the chin support to raise and lower; a bendable portion coupled to the threaded portion; and a geared portion coupled to the bendable portion on an opposite end relative to the threaded portion. The adjustable cervical collar also includes an adjustment knob positioned on the chest piece and coupled to the geared portion of each of the first shaft assembly and the second shaft assembly. The adjustable cervical collar also includes a tightening mechanism configured and adapted to connect to the back piece to the chest piece or the chin support.

This aspect of the invention can have a variety of embodiments. The adjustable cervical collar can further include a strap. The tightening mechanism can be adapted and configured to engage with the strap. The tightening mechanism can be disengaged and re-engaged from the chest piece or the chin support by a user without adjusting a relative positioning of the tightening mechanism and the strap.

The chest piece or the chin support can define a receptable including: a slot; and a first slope and a second slope adjacent to the slot. The adjustable cervical collar can further includes one or more counter-reliefs at an interface between the slot and the slopes.

The back piece can include at least one relief, the relief being configured to provide flexibility to the back piece. The back piece can include a plurality of reliefs.

The tightening mechanism can be located externally to one or more of the chest piece and the back piece.

One or more of the first shaft assembly, the second shaft assembly, and the adjustment knob can be located externally to one or more of the chest piece and the back piece.

Another aspect of the invention provides a method of using the adjustable cervical collar of certain embodiments herein. The method includes (a) positioning the chest piece against the subject's sternum; (b) positioning the back piece on the posterior surface of the subject's neck; and (c) securing a first portion of the tightening mechanism into the receptacle on the chest piece or the chin support.

This aspect of the invention can have a variety of embodiments. The method can further include: (d) adjusting a length of the strap of the tightening mechanism such that a desired tightness is achieved once the first portion of the tightening mechanism is secured into the receptacle.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

DEFINITIONS

The instant invention is most clearly understood with reference to the following definitions.

As used herein, the singular form “a,” “an,” and “the” include plural references unless the context clearly dictates otherwise.

Unless specifically stated or obvious from context, as used herein, the term “about” is understood as within a range of normal tolerance in the art, for example within 2 standard deviations of the mean. “About” can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms “comprises,” “comprising,” “containing,” “having,” and the like can have the meaning ascribed to them in U.S. patent law and can mean “includes,” “including,” and the like.

Unless specifically stated or obvious from context, the term “or,” as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

The present invention provides a novel adjustable cervical collar for stabilizing the head and neck of a patient. The cervical collar of the present invention allows for customizing the fit of the collar to a wide range of patients (including patients with variable neck girths) while minimizing the amount of disruption to the patient during placement and use. Embodiments of the cervical collar 100 according to the present invention include chest piece 1000, a back piece 2000, a chin support 3000, a first and second shaft assembly 4000, and an adjustment knob 1300.

Figure 1:
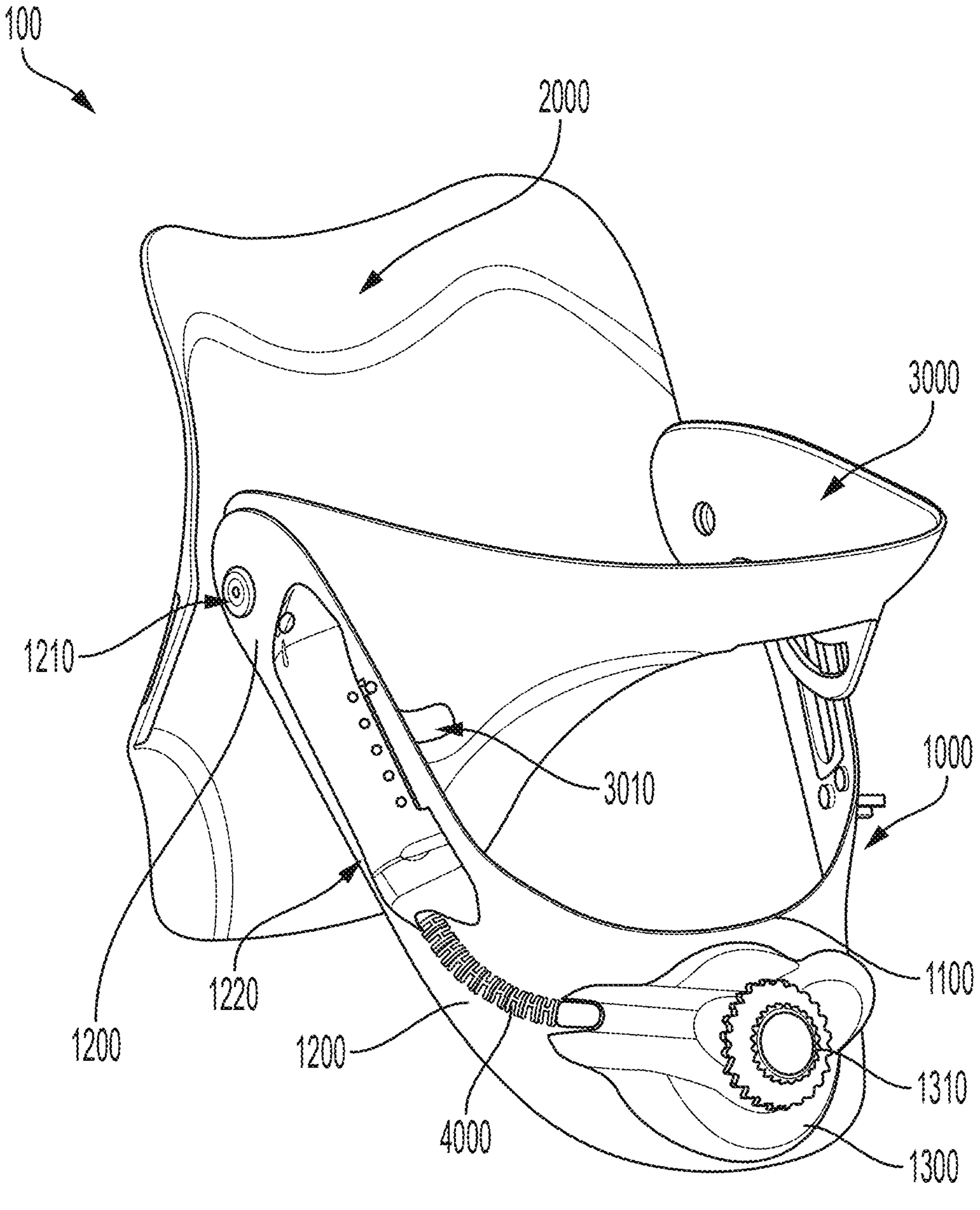
FIG. 1 depicts a three-dimensional view of an exemplary trauma collar as contemplated herein.
Figure 2:
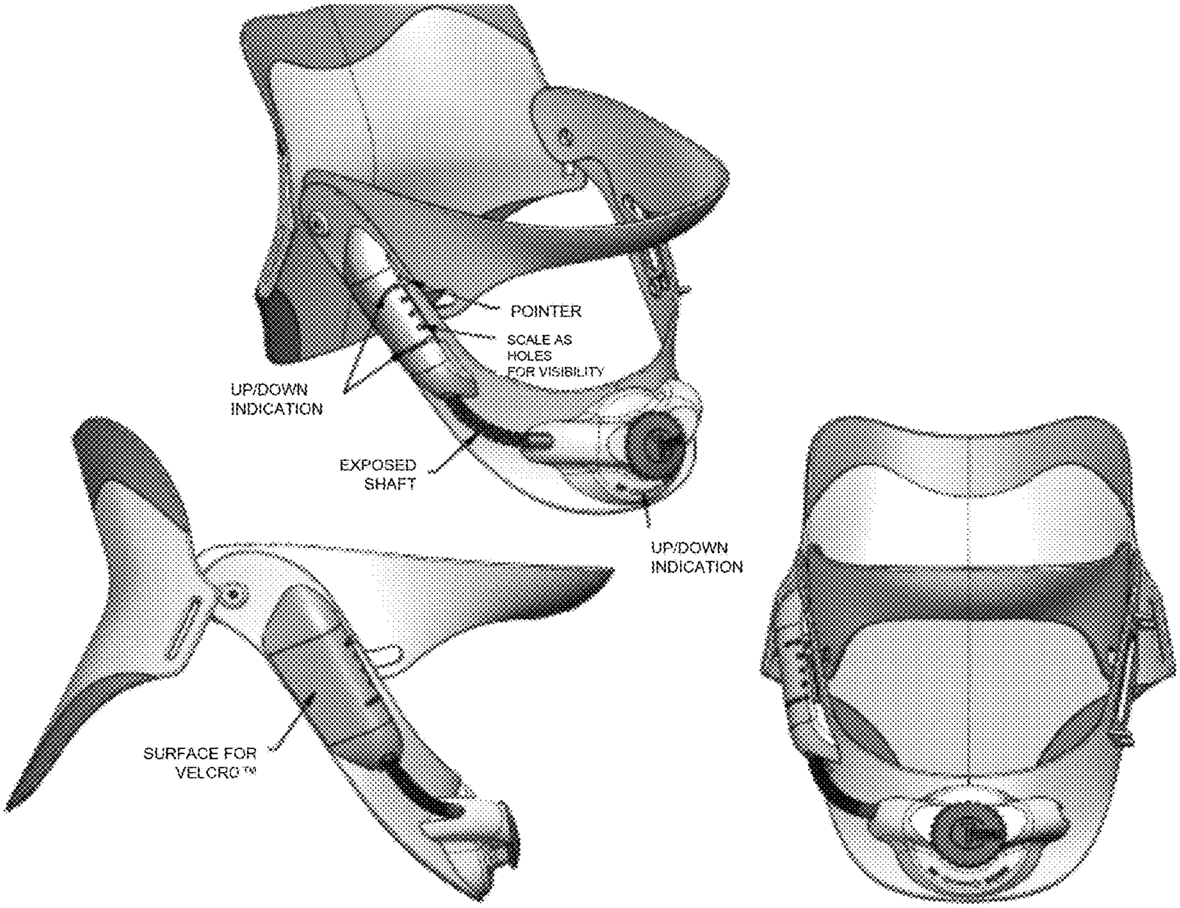
FIG. 2 depicts a three-view drawing of an exemplary trauma collar of the present invention including a front view, a side view and a three-dimensional view.

Referring now to FIG. 1, the chest piece 1000 of the cervical collar includes a sternum support portion 1100 that (e.g., partially) rests on the chest of a subject. Each of the sides of the chest piece 1000 include one or more hinges 1210 (e.g., a screw, a rivet, a stud, a boss, a pin, etc.) or pivoting mechanism that allow the chin support 3000 to pivot up and down.

Figure 3:
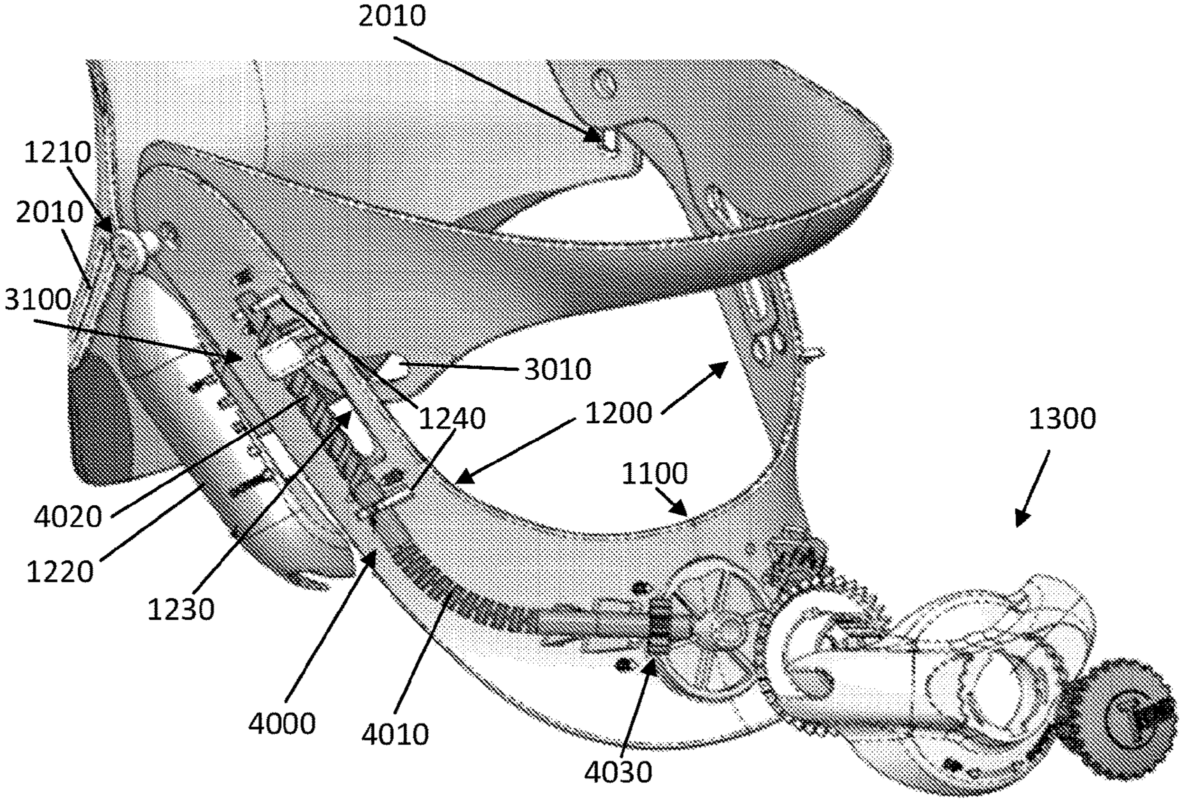
FIG. 3 depicts a zoomed-in view of an exemplary height control system including gears and a support shaft as contemplated herein.

Referring now to FIG. 3, each of the side pieces 1200 of sternum support portion 1100 includes a housing component 1220 for enclosing the engagement point between the chest piece 1000 and the chin support 3000. A housing component 1220 encases a track 1230 that is adapted and configured for receiving a chin position guide 3100 having an internal gear that engages with the helically threaded end 4020 and 4120 (not shown) of each of the two flexible side shaft assemblies 4000 and 4100 (not shown). That is, each of the housings 1220 encase the helically threaded portion 4020 of each of the shafts assemblies 4000 and 4100, and the chin position guide 3100 that tracks along the threaded portion 4020 of the shaft on one end and engages with a track 3010 on the adjacent portion of the chin support. In some embodiments, the chest piece 1000 includes a plurality of bilateral brackets 1240 for securing the first and second shaft assemblies 4000, 4100 to the chest piece 1000 while allowing rotation of the shaft assemblies 4000, 4100 within the brackets 1240.

Figure 5:
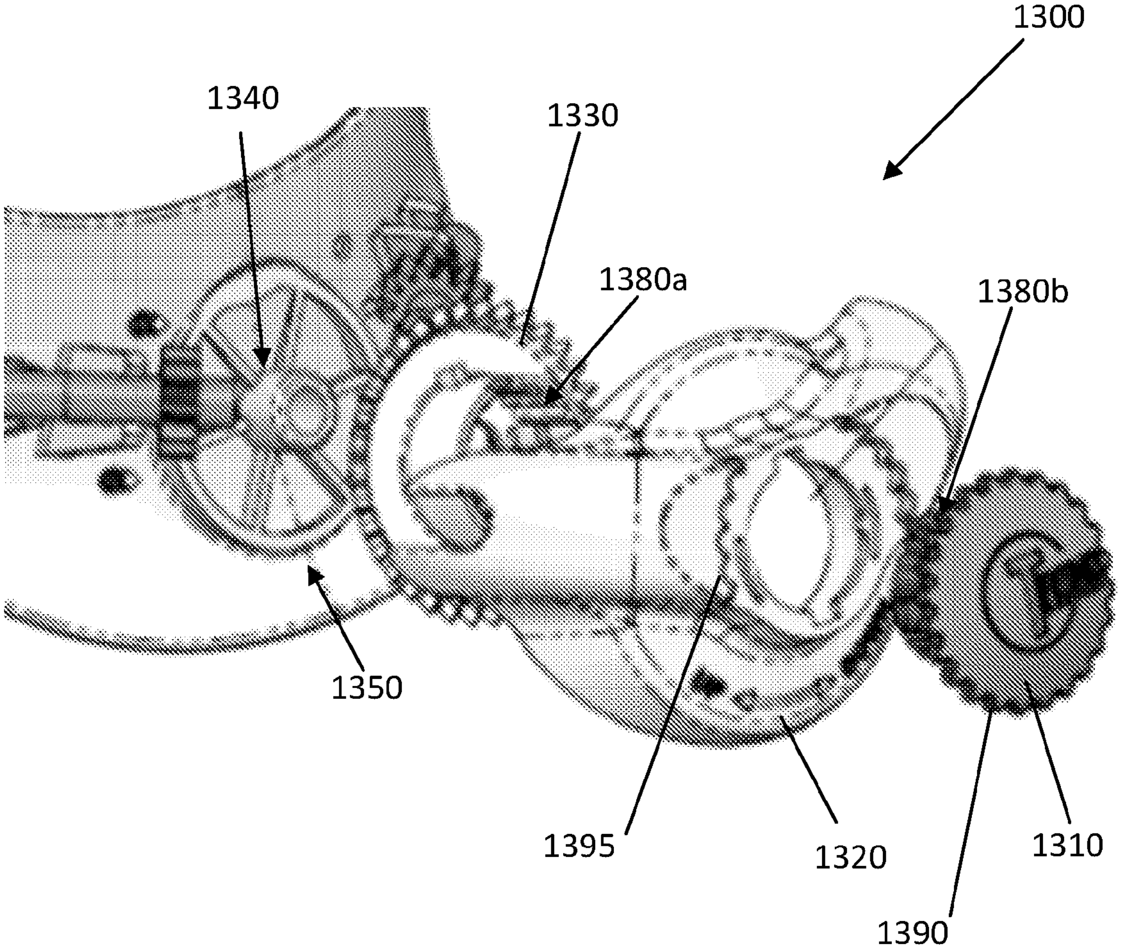
FIG. 5 depicts an exploded view of an adjustment knob assembly as contemplated by the present disclosure.

The chest piece 1000 includes an adjustment knob 1300 on the front surface 1100. Referring now to FIG. 5, the adjustment knob button 1310 is positioned on top of a housing 1320 that encases the geared end 4030 of each of the shaft assemblies 4000. The front surface of the chest piece can include a receiver channel or annular boss 1340 for rotationally supporting the circular bevel gear 1330. The bevel gear 1330 engages with each of the geared portions 4030 of each of the shafts 4000. The top of the bevel gear 1330 can be secured into place by engaging with a track on the bottom of the adjustment assembly housing 1320 that engages with the outer curvature of the internal gear securing it in place. The adjustment knob button 1310 sits on the top of the adjustment assembly housing 1320. In some embodiments, the bevel gear 1330 and the adjustment knob 1310 each have complementary splines 1380 that allow the adjustment knob 1310 to slide axially with respect to the bevel gear 1330. Pressing the adjustment knob 1310 will engage detents 1390 on adjustment knob 1310 with complementary detents 1395 on adjustment assembly housing 1320.

In some embodiments, the chest piece 1000 includes padding or cushioning on the backside for improving the comfort of the subject. The cushioning can include any suitable cushioning material as understood in the art include for example neoprene, foam, fleece, and the like. In some embodiments, the padding is removable. For example, the padding may removably attached to the inner surface of the chin portion using one or more suitable attachment means including for example, snaps, buckles, hook- and loop attachments, and the like. In some embodiments, the chest piece 1000 and/or other components includes a lattice, honeycomb, or other geometry that allows for a plastic piece to deform in response to force and allow ventilation of the subject’s skin below the device.

Referring again to FIGS. 1 and 3, the back piece 2000 of the cervical collar 100 includes a curvature for complementing the back, neck, and skull of a subject. The back piece 2000 supports and stabilizes the cervical spine and base of the skull of the subject. The back piece 2000 includes bilateral slots 2010 for attaching and/or receiving straps (e.g., see strap 1530 of FIG. 9) or other suitable securing implements for securing the back piece 2000 to the sides 1200 of the chest piece 1000. In some embodiments, the straps engage with the outer surface of the housing component on the sides of the chest piece. In some embodiments, the straps engage directly with the outer surface of the sides of the chest piece 1200. In some embodiments, the straps have a split end, wherein one split engages with the outer surface of the housing 1220 and one split engages with the surface of the side piece 1200. The straps may include a patch of loops or hooks that engage with a complementing patch of hooks or loops for securing the back piece to the chest piece with a loop-and-hook attachment with minimal disturbance to the subject.

The straps can be constructed from any suitable material as understood in the art. For example, the strap may be constructed from nylon, polyester, canvas, silicon, and the like.

Referring now to FIGS. 1 and 3, the chin support 3000 of the cervical collar 100 connects to the side pieces 1200 of the chest piece 1000. The chin support 3000 includes a curved shelf 3100 for complementing and supporting the chin of a subject. The position of the chin support 3100 can be adjusted by actuating the adjustment knob 1300 on the front side 1100 of the chest piece 1000.

Figure 4:
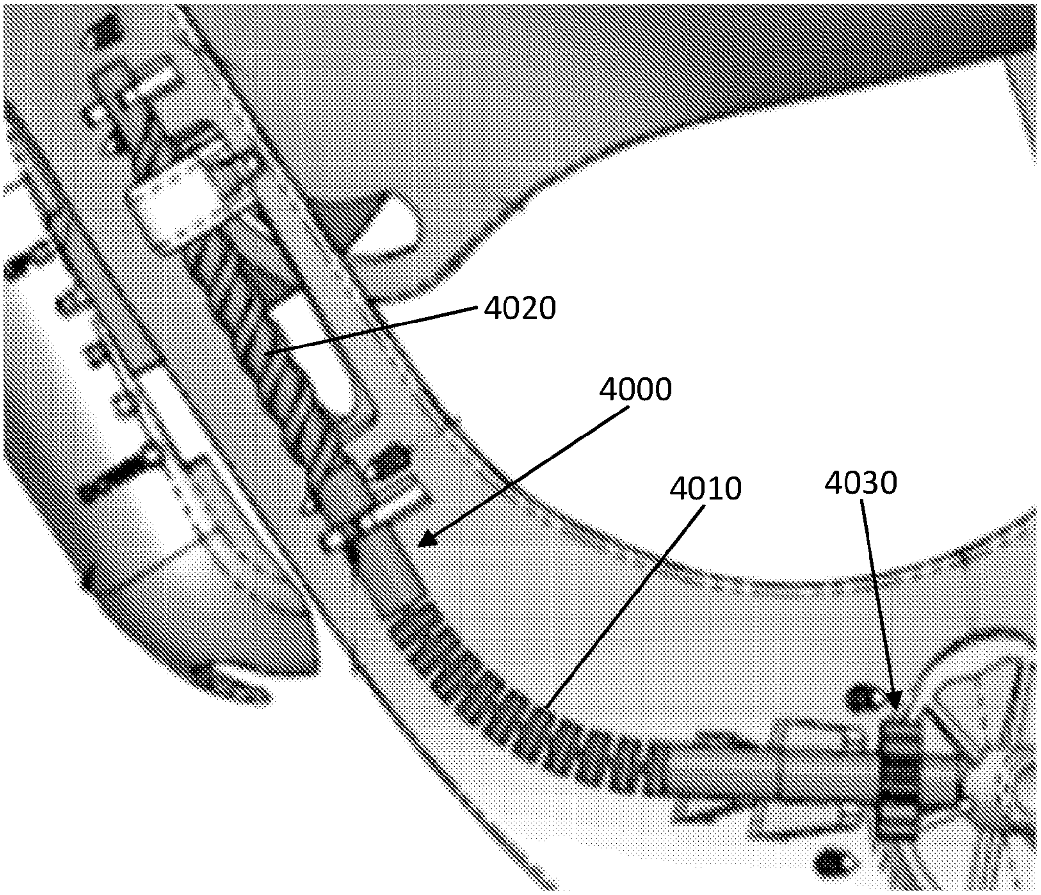
FIG. 4 depicts a zoomed-in view of the shaft assembly as contemplated herein.

Referring now to FIG. 4, embodiments of each of the bilateral shaft assemblies 4000 can include a central flexible joint portion 4010 a threaded end 4020 and a geared end 4030. Embodiments of flexible joint portion 4010 include a corrugated design that has torsional strength for transferring energy from the geared end to the threaded end and driving the chin position guide 3100. The shaft assembly can be constructed from any suitable material as understood in the art. For example, the shaft may be constructed from one or more of nylon, polyvinyl chloride, and the like. In some embodiments, the bilateral shaft assemblies 4000 or at least the central flexible joint portion 4010 is produced using additive manufacturing (also known as 3D printing).

The chest piece 1000, back piece 2000, and chin piece 3000 of the cervical collar 100 can be constructed from any suitable material as understood in the art. Embodiments of the pieces of the cervical collar are constructed from one or more of the following: PVC, nylon, polyester, foam rubber, and the like.

Figure 6A:
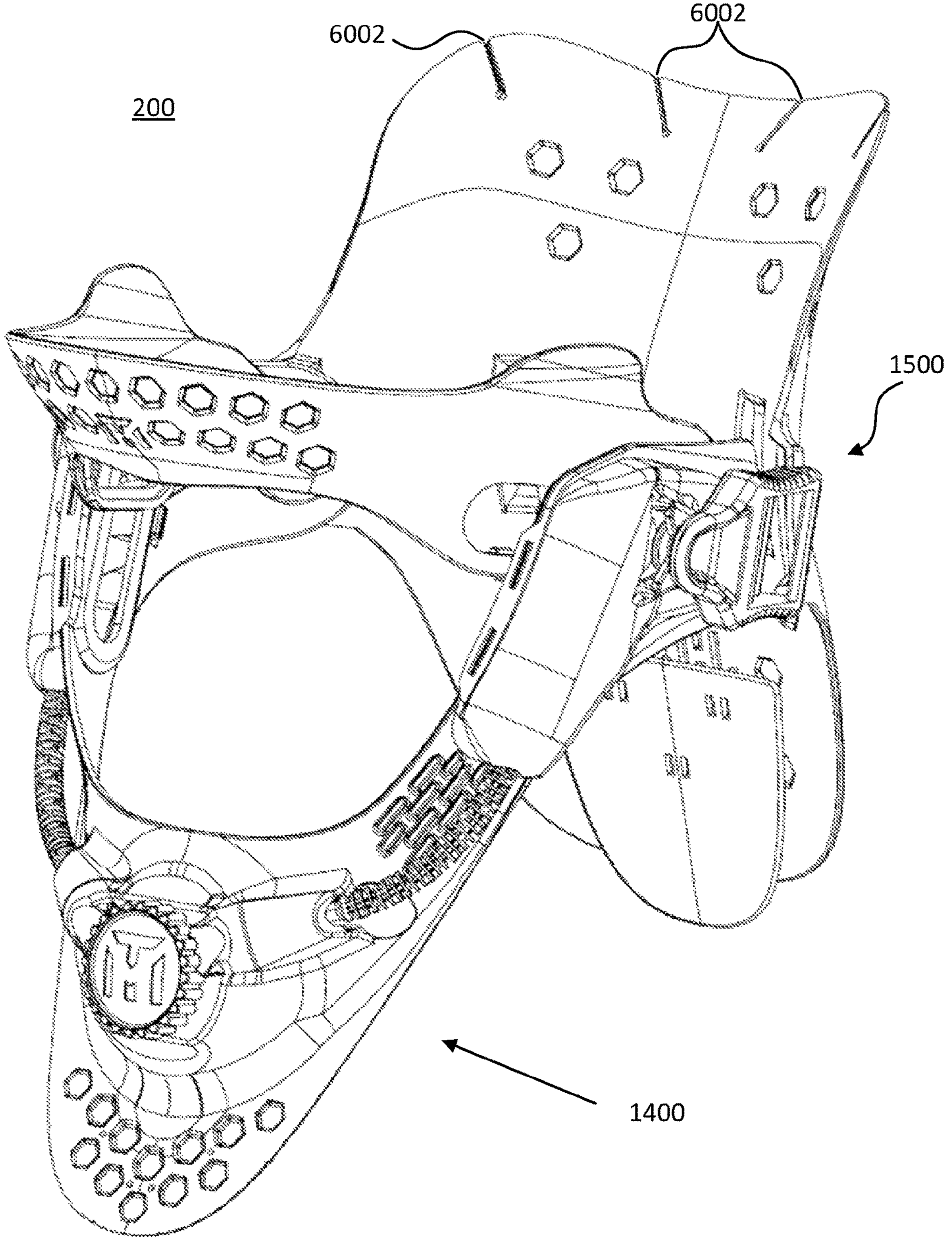
FIGS. 6A-6B depict perspective and frontal three-dimensional views of an exemplary trauma collar as contemplated herein.
Figure 6B:
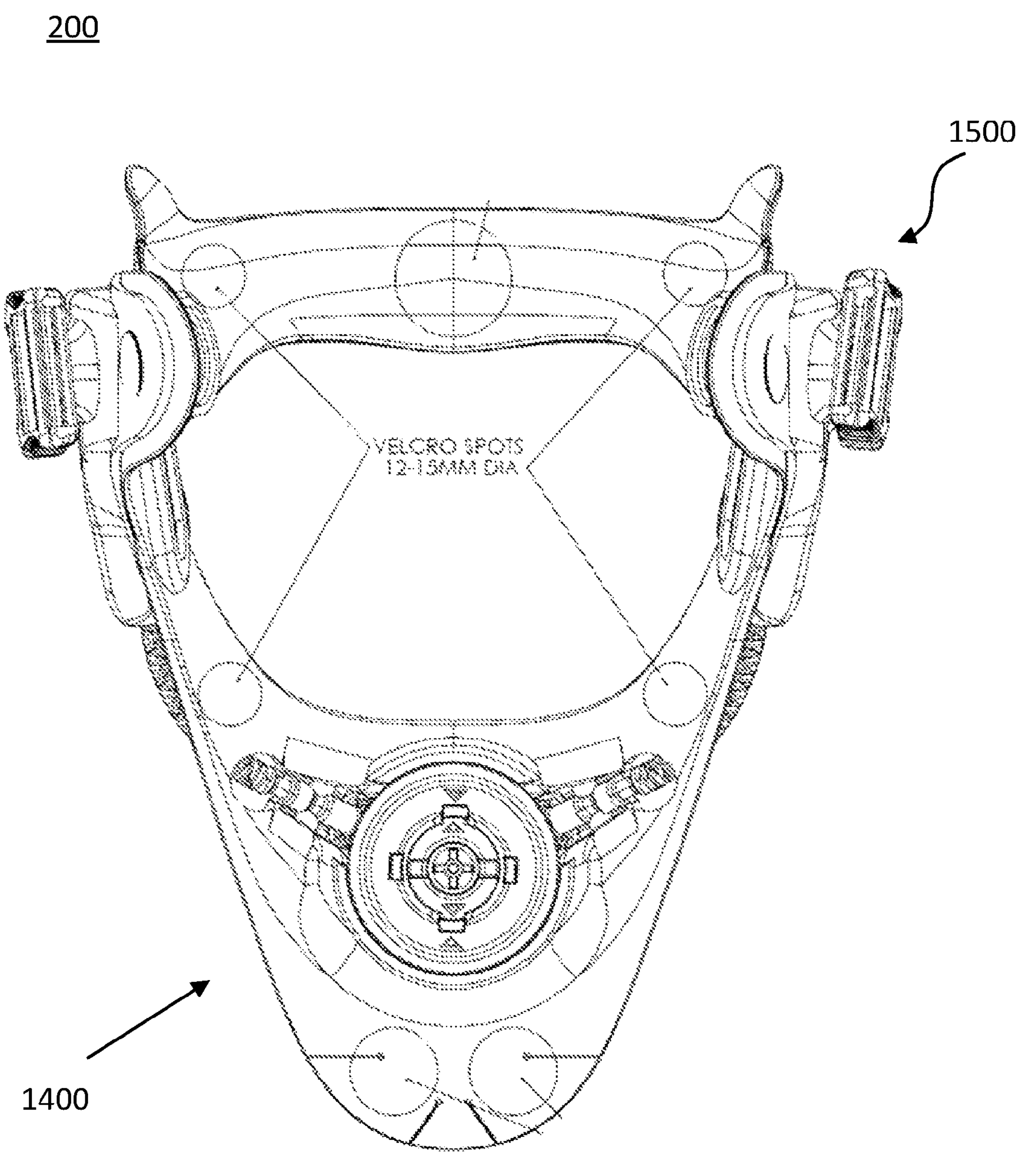

Referring now to FIGS. 6A-6B, perspective and front views of another embodiment of cervical collar 200 are illustrated, respectively. Cervical collar 200 is substantially the same as cervical collar 100, except as described herein (or otherwise obvious from the illustrations). For example, tightening mechanism 1500 is included and adjustment knob 1300 has been replaced with adjustable knob 1400. Reliefs 6002 can allow the back piece 2000 to flex, both circumferentially and dorsally.

Figure 7A:
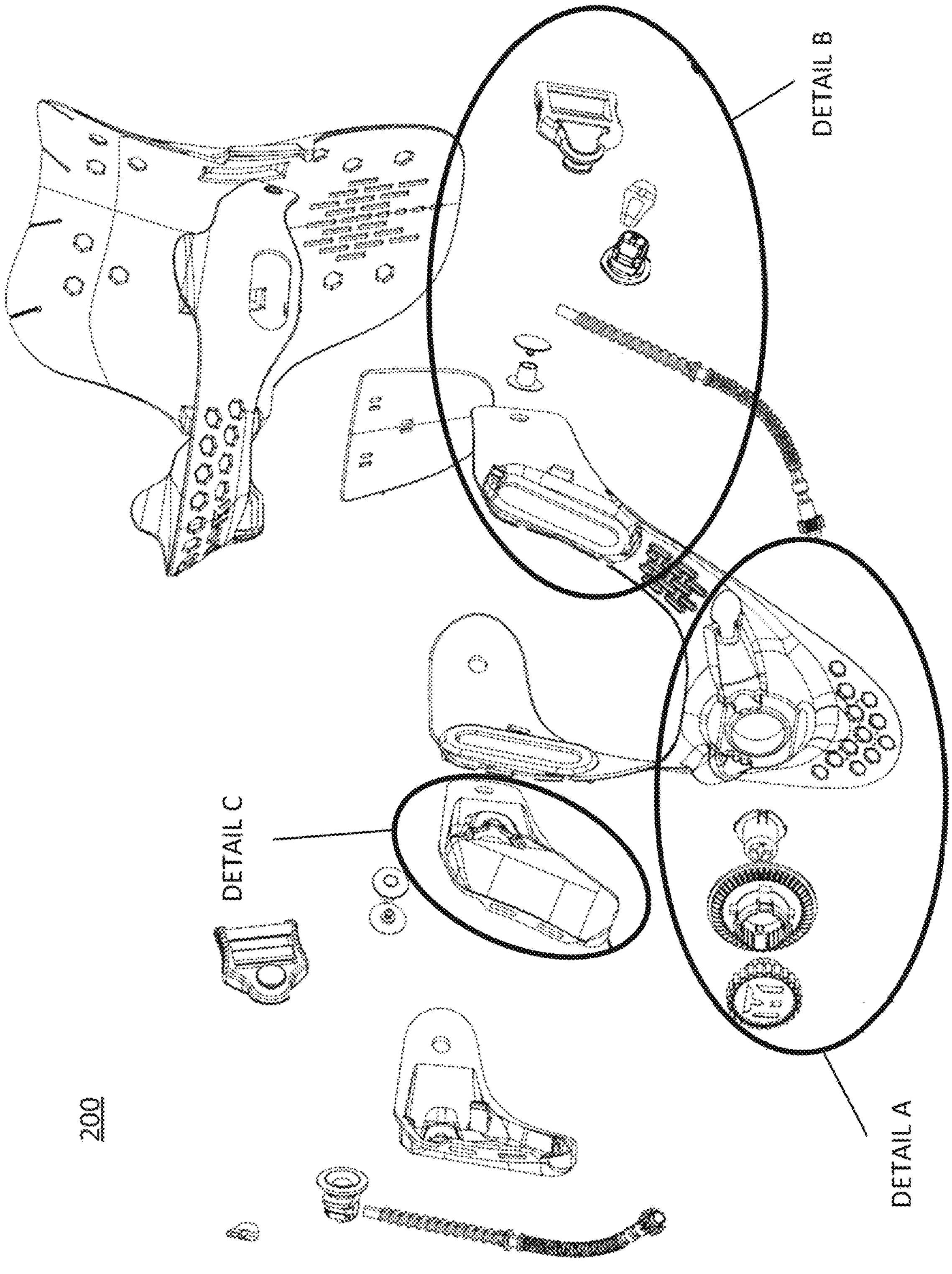
FIG. 7A depicts an exploded view of certain components of an exemplary trauma collar contemplated by the present disclosure.

Referring now to FIG. 7A, a cervical collar 200 is illustrated in an "exploded" view, where individual components can be better illustrated.

Figure 7B:
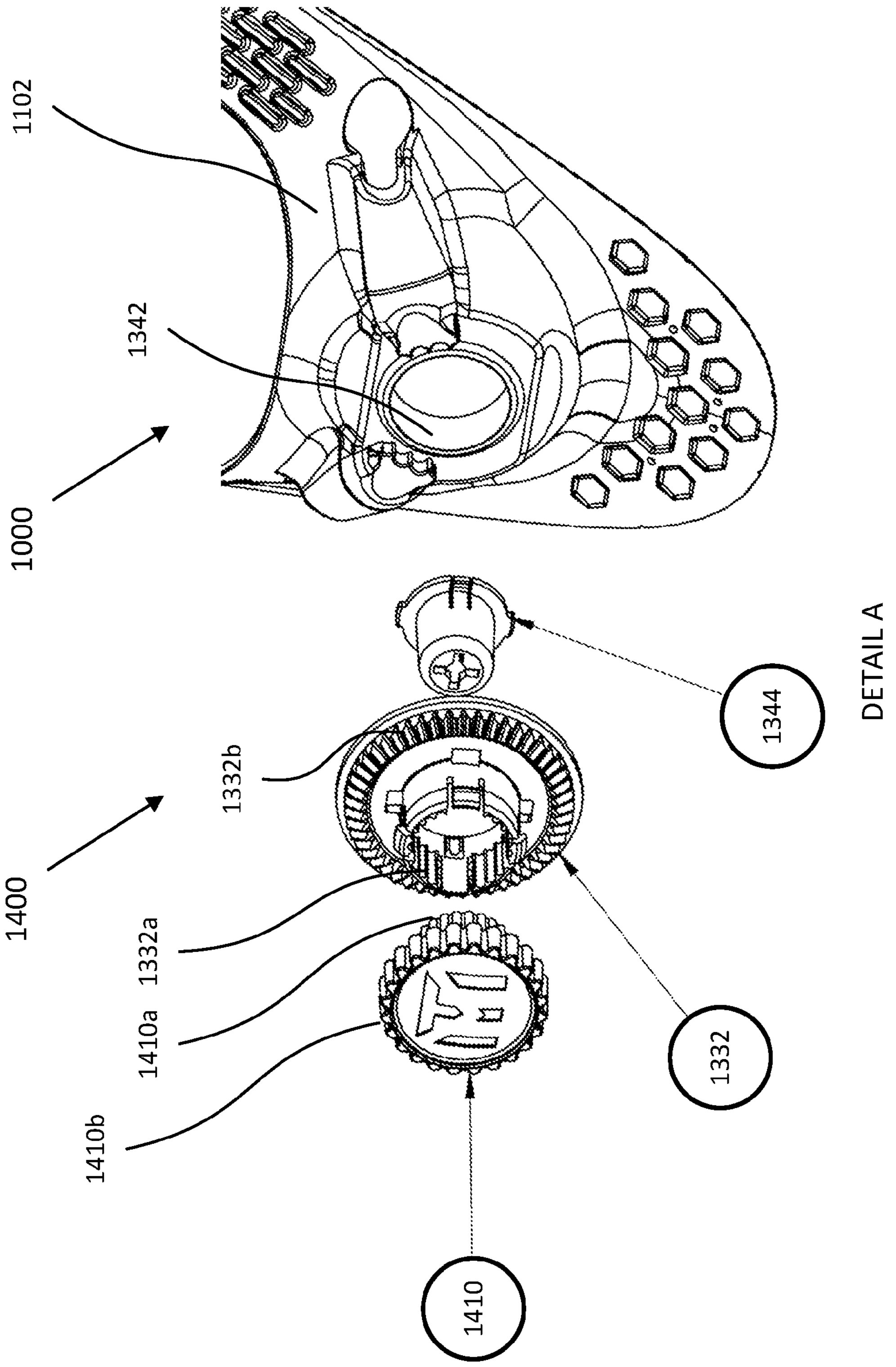
FIG. 7B depicts an exploded view of another adjustment knob assembly as contemplated by the present disclosure.

Referring now to FIG. 7B, a detailed view (i.e., Detail A) of certain components (e.g., adjustment knob 1400) is illustrated. Adjustment knob 1400 includes an adjustment knob button 1410. Adjustment knob button 1410 is illustrated positioned distally from front surface 1102. Adjustment knob button 1410 includes a plurality of gear teeth 1410*a* (e.g., splines) configured to interact with a plurality of teeth 1332*a* (e.g., splines) of circular bevel gear 1332. In other words, adjustment knob button 1410 and circular bevel gear 1332 can have complimentary splines which allow the adjustment knob 1410 to slide axially with respect to the bevel gear 1332.

Circular bevel gear 1332 includes another plurality of teeth 1332*b* (e.g., bevel teeth) configured to engage with each of the geared portions 4030 of each of the shafts 4000. Boss 1344 (e.g., "chin panel) is configured to be inserted through each of circular bevel gear 1332 and adjustment knob button 1410, thereby securing (at least partially) boss 1344, circular bevel gear 1332 and adjustment knob button 1410 such that they rotate together. In one application, when a user (e.g., a patient, a doctor, a nurse, etc.) manually rotates adjustment knob button 1410 using grip 1410*b*, circular bevel gear 1332 rotates thereby causing shafts 4000 to tighten (or loosen depending on the direction of rotation) chest piece 1000 with respect to the other components of cervical collar 200 (e.g., back piece 2000).

Figure 7C:
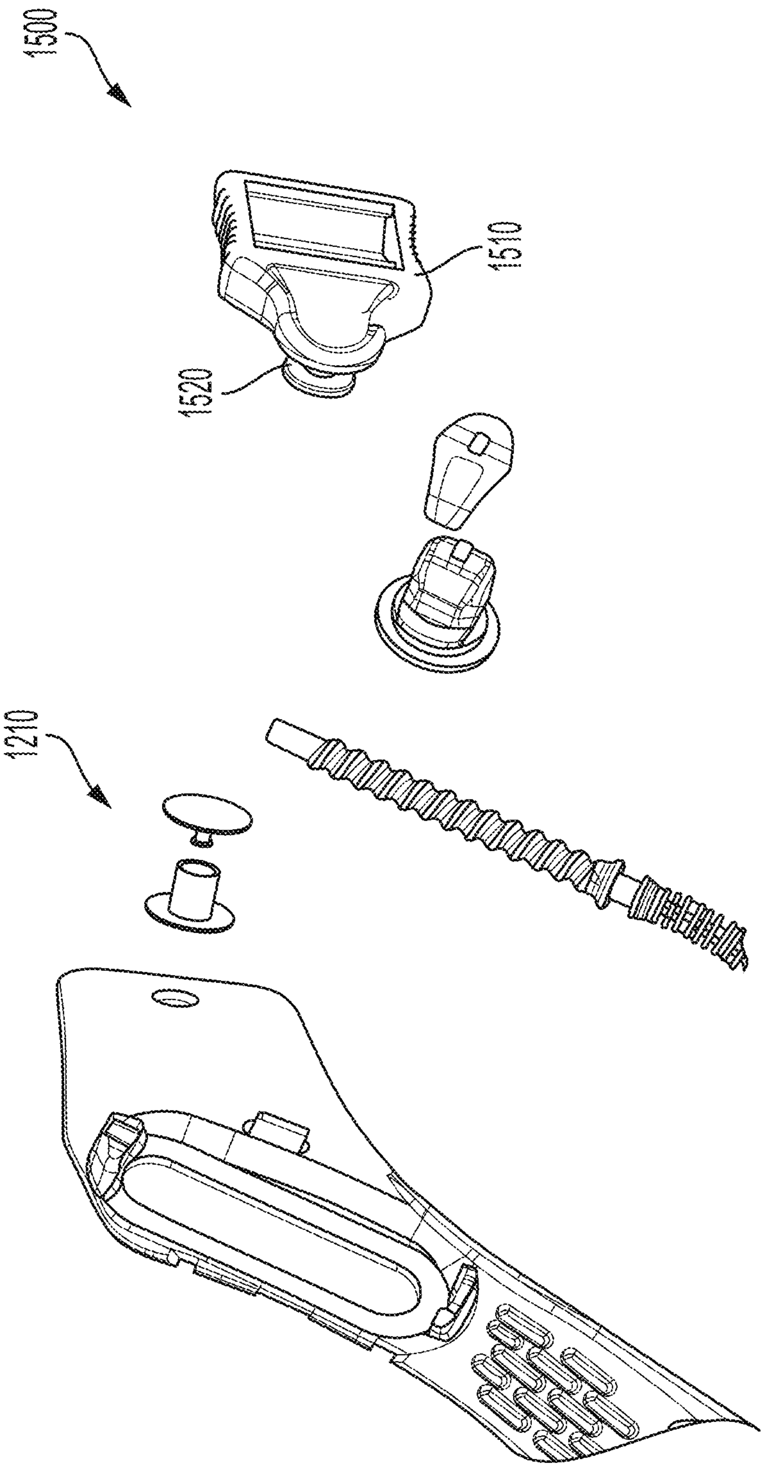
FIG. 7C depicts a detailed view of a tightening mechanism as contemplated by the present disclosure.
Figure 9:
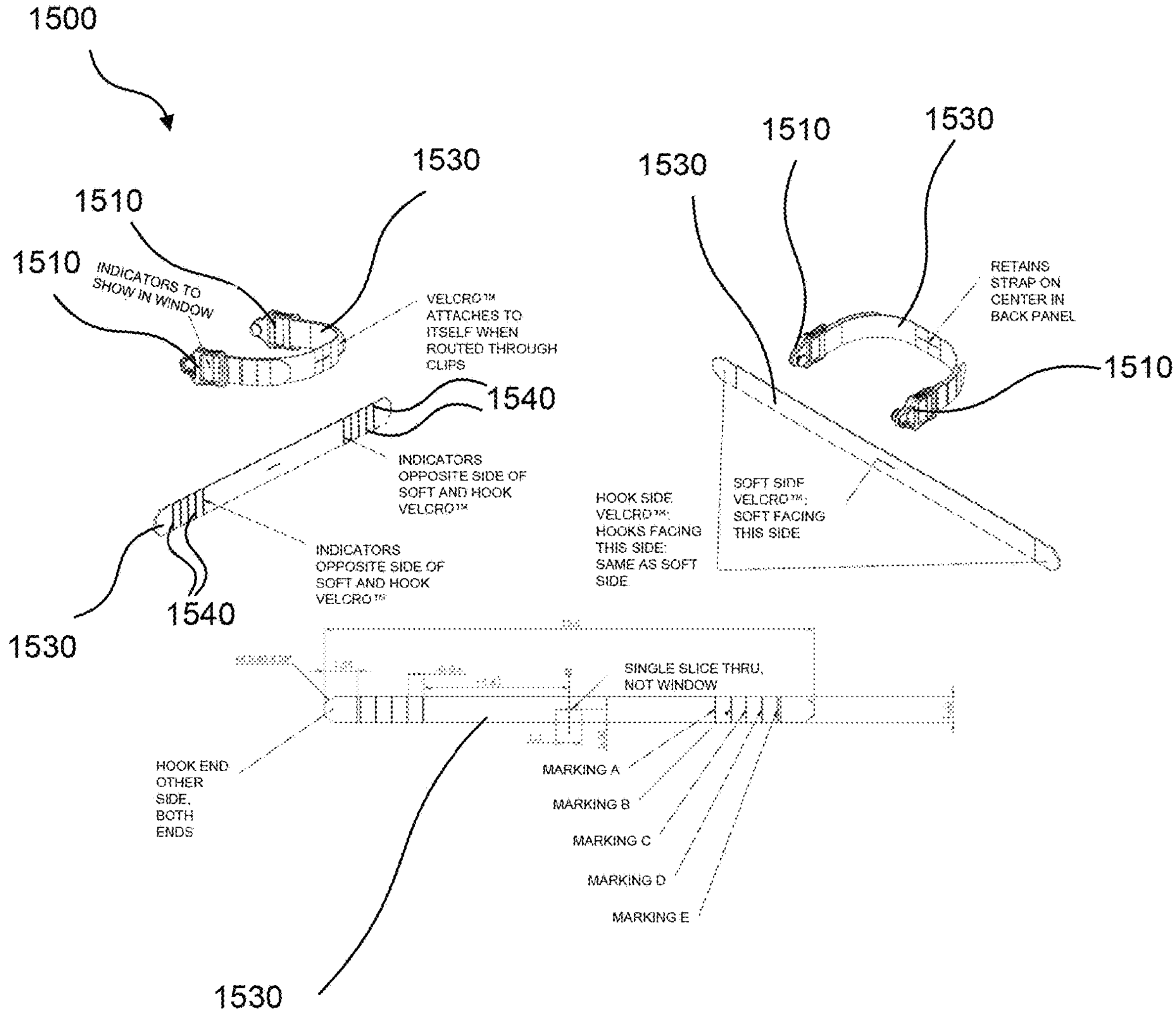
FIG. 9 depicts various detailed views of a tightening mechanism, including an exemplary strap, as contemplated by the present disclosure.

Referring now to FIG. 7C and FIG. 9, various detailed views (e.g., Detail B) of a tightening mechanism 1500 are illustrated. Tightening mechanism 1500 can be configured and adapted to connect to back piece 2000 and chest piece 1000 or chin support 3000 (or both). Tightening mechanism 1500 can include a clip assembly including a first clip portion 1510. First clip portion 1510 can be a housing strap clip configured to receive a strap 1530. In certain embodiments, tightening mechanism 1500 can include a strap 1530 (e.g., an elastic strap, a fabric strap, etc.). Strap 1530 can be configured and adapted to wrap around back piece 2000 and, in some embodiments, connect to another clip assembly or another first clip portion 1510 (e.g., a "mirrored" first clip portion 1510). Strap 1530 can be configured and adapted such that Velcro attaches to itself when routed through clips (e.g., clip portion 1510). Strap 1530 can include indicators 1540 (e.g., markings) to aid a user in initial tightening or adjustments. Tightening mechanism 1500 can include a fastening mechanism 1520 (e.g., including a stud, a boss, a protrusion, a protruded portion, etc.). Fastening mechanism 1520 can be configured to join a first clip portion 1510 and chest piece 1000 and/or chin support 3000 (e.g., directly, indirectly through a receptacle, indirectly through a housing, indirectly through an axle cover, etc.). In one application, a user (e.g., a patient, a doctor, etc.) can "clip" or "secure" a clip assembly onto a portion of chest piece 1000, chin support 3000, or an attached element such that cervical collar 200 is consistently tightened to a defined and/or desired tightness around a patient. In such an embodiment, cervical collar 200 can be tightened to a defined and/or desired tightness irrespective of the number of times clip assembly is "clipped" or "secured" on and off. For example, the first clip portion 1510 can include a buckle trim or slide configured to fix or adjust the length of strap 1530. Strap 1530 can be static or dynamic (i.e., having elasticity under forces applied by a human hand).

Advantageously, embodiments of the invention allow a healthcare provider to adjust the position of the strap relative to first clip portion 1510 (and an opposing clip portion if present) when the device is issued to the patient. The patient can then remove the device (e.g., for bathing) and reliably don the device again without the need to adjust the length of the strap (and the associated tension and positioning of other components) and without the risk of the user over- or under-tightening the strap or any risk that may be associated with the user pulling on a strap coupled to a cervical collar attached to a recovering region of one's body.

Figure 7D:
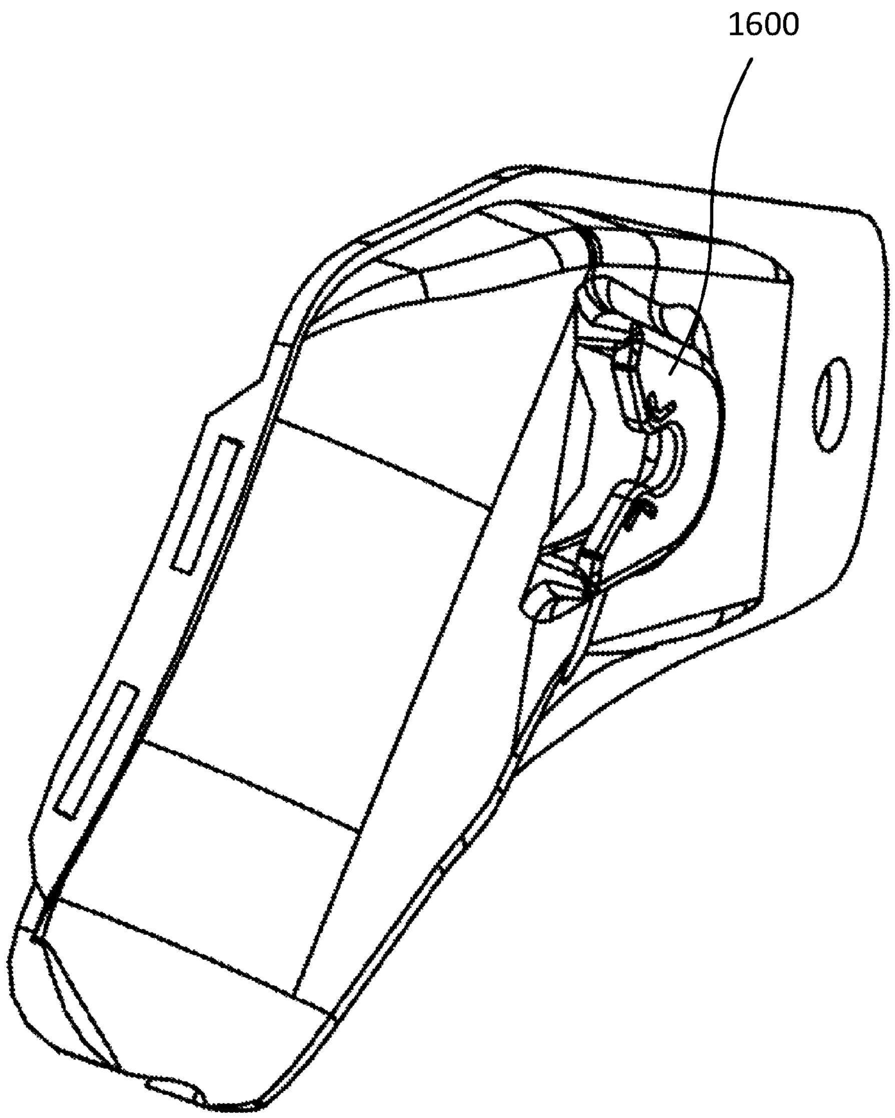
FIG. 7D depicts a detailed view of a receptacle as contemplated by the present disclosure.
Figure 8A:
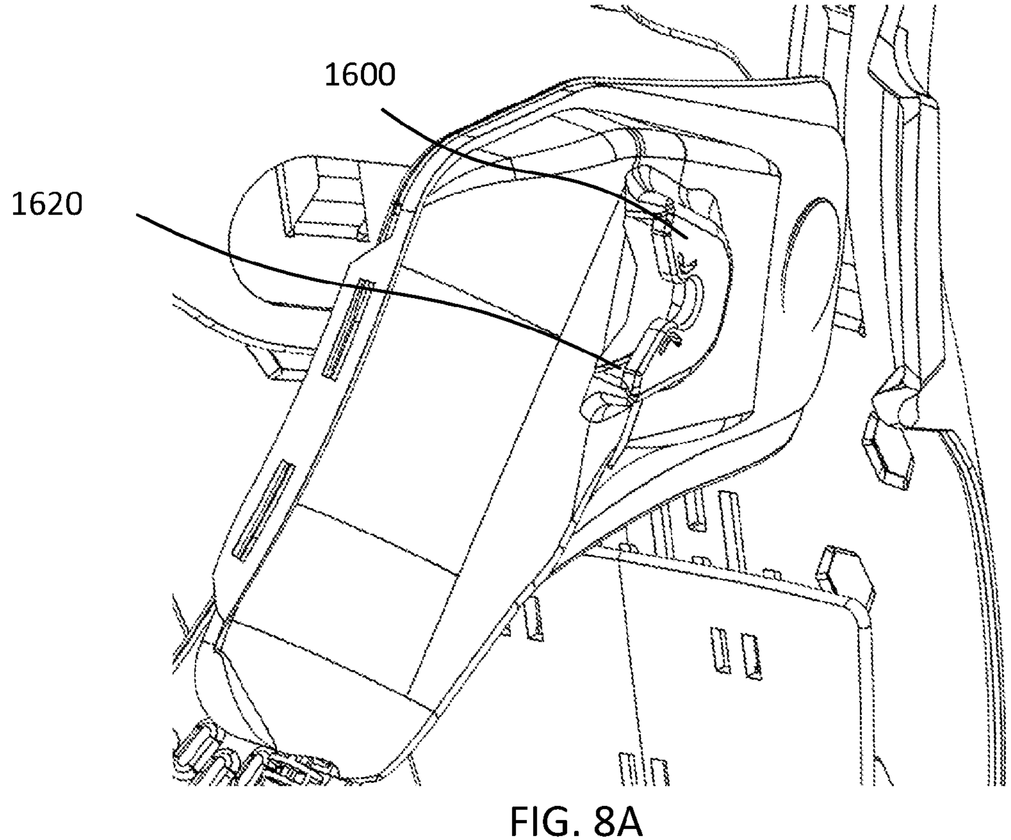
FIGS. 8A-8B depict detailed views of a receptacle as contemplated by the present disclosure.
Figure 8B:
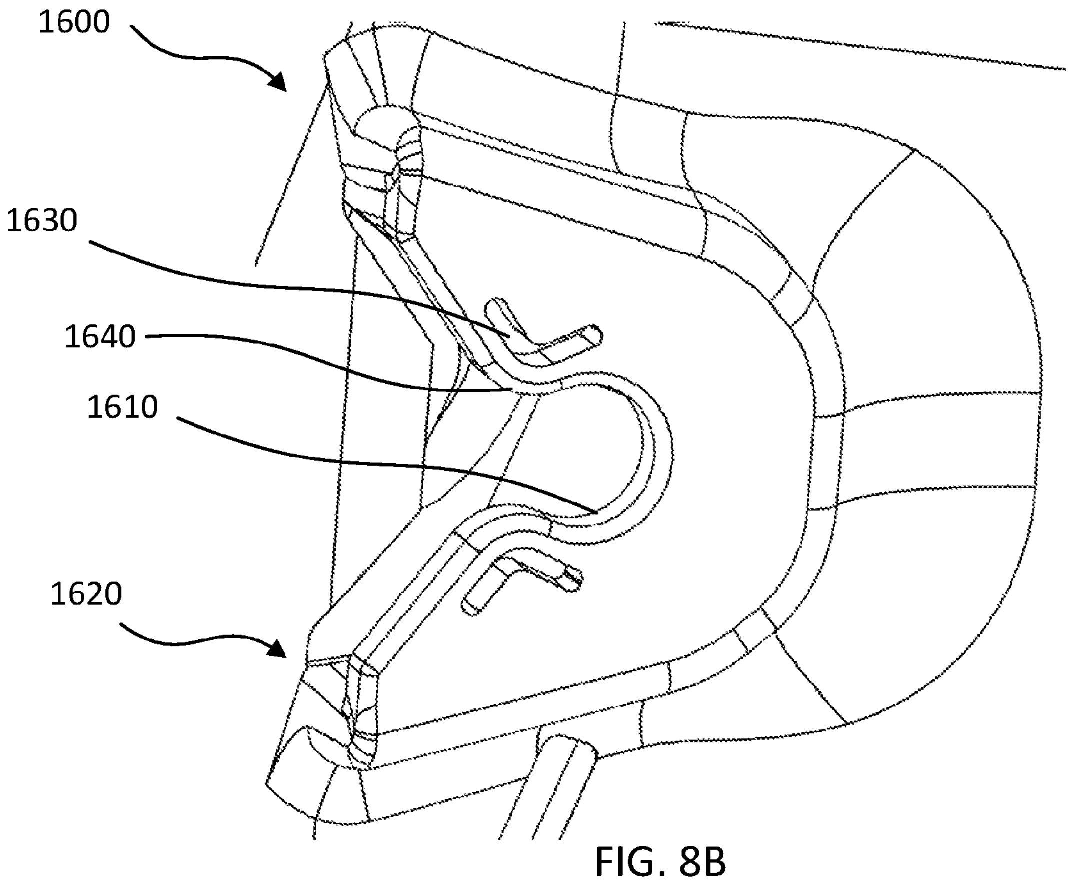

Referring now to FIG. 7D, a receptacle 1600 is illustrated. Receptacle 1600 is configured to receive or interact with at least a portion of tightening mechanism 1500. For example, as illustrated in FIG. 6A, a protruded portion of fastening mechanism 1520 is interconnected with receptacle 1600. Such an embodiment can be better described in connection with FIGS. 8A-8B. A protruded portion of fastening mechanism 1520 can be fitted or slid into a slot portion 1610 of receptacle 1600, thereby securing or fixing at least a portion of tightening mechanism 1500. Receptacle 1600 can be configured and adapted to interact with fastening mechanism 1520. For example, receptacle 1600 can include a tapered portion 1620 that assists a user in connecting fastening mechanism 1520 (of tightening mechanism 1500) to receptacle 1600, e.g., by providing more vertical tolerance for placement of the fastening mechanism 1520 relative to the slot 1610. Receptacle 1600 can also include one or more counter-reliefs 1630 adjacent to a narrow opening 1640 of slot 1610. Such counter-relief can allow the surface of the narrow opening 1640 to flex to accommodate the entry and exit of the fastening mechanism 1520 before returning to its original position to retain the fastening mechanism 1520 within the slot 1610. The fastening mechanism 1520 can also be retained by tension from the strap (e.g., due to elasticity of the strap or other components of the system).

Embodiments of the cervical collar as contemplated herein can be sized to fit a wide range of subjects including an average adult, a large adult, a small adult and/or a child. In some embodiments, the cervical collar includes a universal child size and a universal adult size. Embodiments of the cervical collar include kits having more than one set of straps for adjusting the fit of the cervical collar to accommodate a wide range of adult subjects. In some embodiments, the kit can include more than one back piece and/or more than one chest/chin piece assembly for interchanging parts to fit a wide range of subjects.

Without being bound by theory, Applicant believes that positioning of adjustment components such as first and second shaft assembly 4000, adjustment knob 1300, and/or strap 1530 external to the chest piece 1000, back piece 2000, and/or chin support 3000 enables accommodation of a wide variety of neck girths. In particular, the central flexible joint portion 4010 can accommodate varying angles when the chest piece 1000 is flexed acutely or obtusely.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. An adjustable cervical collar comprising:
- a chest piece adapted and configured to rest against a subject's sternum;
- a back piece adapted and configured to rest on a posterior surface of the subject's neck and couple to the chest piece; and
- a chin support movably coupled to the chest piece;
- a first shaft assembly and a second shaft assembly each rotatably mounted on a opposing lateral regions of the chest piece, the first shaft assembly and a second shaft assembly each comprising:
  - a helically threaded portion engaged with the chin support such that rotation of the helically threaded shaft causes the chin support to raise and lower;
  - a bendable portion coupled to the helically threaded portion; and
  - a geared portion coupled to the bendable portion on an opposite end relative to the helically threaded portion;
- an adjustment knob positioned on the chest piece and coupled to the geared portion of each of the first shaft assembly and the second shaft assembly;
- a tightening mechanism configured and adapted to connect to the back piece to the chest piece or the chin support; and
- a strap;
- wherein:
  - the tightening mechanism is adapted and configured to engage with the strap; and
  - the tightening mechanism can be disengaged and re-engaged from the chest piece or the chin support by a user without adjusting a relative positioning of the tightening mechanism and the strap;
  - the chest piece or the chin support define at least one receptacle, each receptacle comprising:
    - a slot; and
    - a first slope and a second slope adjacent to the slot; and
  - each receptacle is unbound ventrally beyond the first slope and the second slope; and
- the tightening mechanism comprises a male member sized to be received within the slot of one of the receptacle.

2. The adjustable cervical collar of claim 1, wherein the adjustment knob is coupled to a bevel gear complementary to the geared portion of the first shaft assembly and the second shaft assembly.

3. The adjustable cervical collar of claim 2, wherein the bevel gear and the adjustment knob each comprise complementary splines that allow the adjustment knob to slide axially with respect to the bevel gear.

4. The adjustable cervical collar of claim 1, wherein the adjustment knob and the chest piece further comprise complementary detents, wherein the complementary detents can be:
- engaged to lock by moving the adjustment knob toward the subject's sternum; and disengaged to allow rotation by moving the adjustment knob away from the subject's sternum.

5. The adjustable cervical collar of claim 1, wherein the back piece includes at least one relief, the relief being configured to provide flexibility to the back piece.

6. The adjustable cervical collar of claim 5, wherein the back piece includes a plurality of reliefs.

7. The adjustable cervical collar of claim 1, wherein one or more of the first shaft assembly, the second shaft assembly, and the adjustment knob is located externally to one or more of the chest piece and the back piece.

8. An adjustable cervical collar comprising:
- a chest piece adapted and configured to rest against a subject's sternum;
- a back piece adapted and configured to rest on a posterior surface of the subject's neck and couple to the chest piece;
- a chin support movably coupled to the chest piece;

a first shaft assembly and a second shaft assembly each rotatably mounted on a opposing lateral regions of the chest piece, the first shaft assembly and a second shaft assembly each comprising:

a threaded portion engaged with the chin support such that rotation of a threaded shaft causes the chin support to raise and lower;

a bendable portion coupled to the threaded portion; and a geared portion coupled to the bendable portion on an opposite end relative to the threaded portion;

an adjustment knob positioned on the chest piece and coupled to the geared portion of each of the first shaft assembly and the second shaft assembly;

a tightening mechanism configured and adapted to connect to the back piece to the chest piece or the chin support; and a strap;

wherein:

the tightening mechanism is adapted and configured to engage with the strap; and the tightening mechanism can be disengaged and re-engaged from the chest piece or the chin support by a user without adjusting a relative positioning of the tightening mechanism and the strap;

the chest piece or the chin support define at least one receptacle, each receptacle comprising:

a slot; and a first slope and a second slope adjacent to the slot; and each receptacle is unbound ventrally beyond the first slope and the second slope; and the tightening mechanism comprises a male member sized to be received within the slot of one of the receptacle.

9. The adjustable cervical collar of claim 8, further comprising one or more counter-reliefs at an interface between the slot and the slopes.

10. The adjustable cervical collar of claim 8, wherein the back piece includes at least one relief, the relief being configured to provide flexibility to the back piece.

11. The adjustable cervical collar of claim 10, wherein the back piece includes a plurality of reliefs.

12. The adjustable cervical collar of claim 8, wherein the tightening mechanism is located externally to one or more of the chest piece and the back piece.

13. The adjustable cervical collar of claim 8, wherein one or more of the first shaft assembly, the second shaft assembly, and the adjustment knob is located externally to one or more of the chest piece and the back piece.

14. A method of using the adjustable cervical collar of claim 8, the method comprising:

(a) positioning the chest piece against the subject's sternum;

(b) positioning the back piece on the posterior surface of the subject's neck; and (c) securing a first portion of the tightening mechanism into the receptacle on the chest piece or the chin support.

15. The method of claim 14 further comprising:

(d) adjusting a length of the strap of the tightening mechanism such that a desired tightness is achieved once the first portion of the tightening mechanism is secured into the receptacle.

* * * * *